United States Patent
Agee et al.

[11] Patent Number: 6,155,039
[45] Date of Patent: Dec. 5, 2000

[54] SYNTHESIS GAS PRODUCTION SYSTEM AND METHOD

[75] Inventors: Kenneth L. Agee; Mark A. Agee; Larry J. Weick, all of Tulsa, Okla.; Elliot L. Trepper, Arvada, Colo.

[73] Assignee: Syntroleum Corporation, Tulsa, Okla.

[21] Appl. No.: 09/439,938

[22] Filed: Nov. 12, 1999

Related U.S. Application Data

[62] Division of application No. 08/879,553, Jun. 20, 1997, abandoned.
[60] Provisional application No. 60/020,092, Jul. 21, 1996.

[51] Int. Cl.[7] ............................................. F02C 3/28
[52] U.S. Cl. ........................................ 60/39.02; 60/39.12
[58] Field of Search .................................. 60/39.02, 39.06, 60/39.12, 39.465, 723

[56] References Cited

U.S. PATENT DOCUMENTS

| | | |
|---|---|---|
| 1,746,464 | 2/1930 | Fischer et al. . |
| 1,798,288 | 3/1931 | Wietzel et al. . |
| 2,247,087 | 6/1941 | Herbert . |
| 2,468,494 | 4/1949 | Griffin, Jr. . |
| 2,472,427 | 6/1949 | Johnson . |
| 2,486,243 | 10/1949 | Atwell . |
| 2,500,533 | 3/1950 | Friedman . |
| 2,518,337 | 8/1950 | Krebs . |
| 2,552,308 | 5/1951 | Buchmann et al. . |
| 2,552,737 | 5/1951 | Rees . |
| 2,579,828 | 12/1951 | Johnson . |
| 2,583,611 | 1/1952 | Sullivan, Jr. . |
| 2,615,911 | 10/1952 | Williams . |
| 2,617,709 | 11/1952 | Cornell . |
| 2,640,843 | 6/1953 | Hill et al. . |
| 2,660,032 | 11/1953 | Rosenthal . |
| 2,686,195 | 8/1954 | McAdams et al. . |
| 2,697,655 | 12/1954 | Dickinson et al. . |
| 3,549,335 | 12/1970 | Grotz, Jr. . |
| 3,673,218 | 6/1972 | Cairns et al. . |

(List continued on next page.)

FOREIGN PATENT DOCUMENTS

| | | |
|---|---|---|
| 83575/82 | 12/1982 | Australia . |
| 17172/92 | 12/1992 | Australia . |
| 29777/92 | 6/1993 | Australia . |
| 414019 | 2/1936 | Belgium . |
| 212755 | 3/1987 | European Pat. Off. . |
| 103914 | 1/1988 | European Pat. Off. . |
| 261771 | 3/1988 | European Pat. Off. . |
| 0497425A1 | 1/1992 | European Pat. Off. . |
| 516441 | 12/1992 | European Pat. Off. . |
| 601886 | 6/1994 | European Pat. Off. . |

(List continued on next page.)

OTHER PUBLICATIONS

Provisional Application Serial No. 60/020,092 entitled "Synthesis Gas Production System", Jun. 21, 1996.
Patent Application USSN 08/814,780 entitled "Turbine–Powered, Synthesis–Gas System and Method" by K. Agee, et al., Mar. 10, 1997.
Patent Application USSN 08/879,552 entitled "Fixed–Bed, CatalyticReactor and Method" by K. Agee, Jun. 20, 1997.
Patent Application USSN 08/679,402 entitled "Process for Converting Gas to Liquids" by J.R. Wolflick, et al., Jul. 9, 1996.

(List continued on next page.)

*Primary Examiner*—Louis J. Casaregola
*Attorney, Agent, or Firm*—Baker Botts L.L.P.

[57] ABSTRACT

A synthesis gas production system (302) incudes a gas turbine (310) having a compressor (312) with an autothermal reformer (308) between the compressor (312) and the turbine (314). The system (302) may include a separator (326) for removing a portion of the mass exiting the compressor (312) prior to its delivery to the autothermal reformer (308). Gaseous light hydrocarbons are delivered to the autothermal reformer (308) through conduit (330) and may be selectively controlled with a valve (331). Synthesis gas production system (302) may be used with a methanol process, ammonia process, a Fischer-Tropsch process (304), or other process involving synthesis gas.

5 Claims, 4 Drawing Sheets

U.S. PATENT DOCUMENTS

| | | |
|---|---|---|
| 3,765,167 | 10/1973 | Rudolph et al. ..................... 60/39.02 |
| 3,866,411 | 2/1975 | Marion et al. . |
| 3,868,817 | 3/1975 | Marion et al. . |
| 3,920,579 | 11/1975 | Slater . |
| 3,959,972 | 6/1976 | Rudolph et al. . |
| 3,986,349 | 10/1976 | Egan . |
| 4,048,250 | 9/1977 | Garwood et al. . |
| 4,074,981 | 2/1978 | Slater . |
| 4,075,831 | 2/1978 | McGann . |
| 4,092,825 | 6/1978 | Egan . |
| 4,121,912 | 10/1978 | Barber et al. . |
| 4,132,065 | 1/1979 | McGann . |
| 4,147,456 | 4/1979 | Klass . |
| 4,158,680 | 6/1979 | McGann . |
| 4,184,322 | 1/1980 | Paull et al. . |
| 4,309,359 | 1/1982 | Pinto . |
| 4,315,893 | 2/1982 | McCallister . |
| 4,338,292 | 7/1982 | Duranleau . |
| 4,341,069 | 7/1982 | Bell et al. . |
| 4,372,920 | 2/1983 | Zardi . |
| 4,423,022 | 12/1983 | Albano et al. . |
| 4,423,156 | 12/1983 | Bussemeier et al. . |
| 4,434,613 | 3/1984 | Stahl . |
| 4,481,305 | 11/1984 | Jorn et al. . |
| 4,492,085 | 1/1985 | Sahl et al. . |
| 4,522,939 | 6/1985 | Minderhoud et al. . |
| 4,524,581 | 6/1985 | Cascone et al. . |
| 4,528,811 | 7/1985 | Stahl . |
| 4,549,396 | 10/1985 | Garwood et al. . |
| 4,579,985 | 4/1986 | Minderhoud et al. . |
| 4,579,986 | 4/1986 | Sie . |
| 4,587,008 | 5/1986 | Minderhoud et al. . |
| 4,618,451 | 10/1986 | Gent . |
| 4,640,766 | 2/1987 | Post et al. . |
| 4,678,723 | 7/1987 | Wertheim . |
| 4,681,701 | 7/1987 | Sie . |
| 4,732,092 | 3/1988 | Gould . |
| 4,755,536 | 7/1988 | Mauldin et al. . |
| 4,778,826 | 10/1988 | Jezl et al. . |
| 4,833,140 | 5/1989 | Weber et al. . |
| 4,833,170 | 5/1989 | Agee . |
| 4,869,887 | 9/1989 | Van Dijk . |
| 4,894,205 | 1/1990 | Westerman et al. . |
| 4,919,909 | 4/1990 | Lesur et al. . |
| 4,946,477 | 8/1990 | Perka et al. . |
| 4,946,660 | 8/1990 | Denny et al. . |
| 4,973,453 | 11/1990 | Agee . |
| 4,999,029 | 3/1991 | Lueth et al. . |
| 5,026,934 | 6/1991 | Bains et al. . |
| 5,028,634 | 7/1991 | Fiato . |
| 5,048,284 | 9/1991 | Lywood et al. . |
| 5,080,872 | 1/1992 | Jezl et al. . |
| 5,126,377 | 6/1992 | Bessell . |
| 5,177,114 | 1/1993 | Van Dijk et al. . |
| 5,245,110 | 9/1993 | Van Dijk et al. . |
| 5,295,350 | 3/1994 | Child et al. . |
| 5,295,356 | 3/1994 | Billy . |
| 5,324,335 | 6/1994 | Benham et al. . |
| 5,472,986 | 12/1995 | Van Dijk . |
| 5,477,924 | 12/1995 | Pollack . |
| 5,500,449 | 3/1996 | Benham et al. . |
| 5,504,118 | 4/1996 | Benham et al. . |
| 5,506,272 | 4/1996 | Benham et al. . |
| 5,520,891 | 5/1996 | Lee . |
| 5,543,437 | 8/1996 | Benham et al. . |
| 5,733,941 | 3/1998 | Waycuilis . |
| 5,861,441 | 1/1999 | Waycuilis . |

FOREIGN PATENT DOCUMENTS

| | | |
|---|---|---|
| 503482 | 7/1994 | European Pat. Off. . |
| 501331 | 6/1995 | European Pat. Off. . |
| 871230 | 4/1942 | France . |
| 922493 | 4/1947 | France . |
| 1537457 | 8/1968 | France . |
| 60007929 | 1/1985 | Japan . |
| 04364142 | 12/1992 | Japan . |
| 2103647 | 8/1984 | United Kingdom . |
| 2139644 | 11/1984 | United Kingdom . |
| WO86/05775 | 10/1986 | WIPO . |
| WO93/06041 | 9/1992 | WIPO . |
| WO95/24961 | 9/1995 | WIPO . |
| WO97/33847 | 9/1997 | WIPO . |

OTHER PUBLICATIONS

Patent Application USSN 08/744032 entitled "Gas Conversion Process Using a Chain–Limiting Reactor" by G. Beer, Nov. 5, 1996.

Patent Application USSN 08/600,565 entitled "Hydrocarbon Gas Conversion System and Process for Producing a Synthetic Hydrocarbon Liquid" by J.J. Waycuilis, Feb. 13,1996.

Patent Application USSN 08/800,642 entitled "Combusting a Hydrocarbon Gas to Produce a Reformed Gas" by J.J. Waycuilis, Feb. 14,1997.

"Kinetics of the Fischer–Tropsch Synthesis using a Nitrogen–Rich Gas," T. Knutze et al., Oil Gas–European magazine, Jan. 1995, pp. 19–24, Jan. 1995.

"A New Concept for the Production of Liquid Hydrocarbons from Natural Gas;" K. Hedden, et al.; Oil Gas–European magazine, Mar. 1994, pp. 42–44, Mar. 1994.

"Production of Synthesis Gas by Catalytic Partial Oxidation of Methane with Air," A. Jess, et al.; Oil Gas—European magazine, pp. 23–27, Apr. 1994.

"Improve Syngas Production using Autothermal Reforming," T.S. Christensen, Hydrocarbon Processing, pp. 39–46, Mar. 1994.

"Economical Utilization of Natural Gas to Produce Synthetic Petroleum Liquids;" K. Agee, et al.; Seventy–fifth Annual GPA Convention; Denver, Colorado, Mar. 11–13, 1996.

"The Mother Lode of Natural Gas," R. Monasterskky, 150 Science News 298, 1996.

PCT Search Report, for PCT/US 97/03729, filed Mar. 10, 1997, Jun. 11, 1997.

"The Fischer–Tropsch Synthesis," R.B. Anderson; Academic Press, Inc.; NY, 1984, pp. 186–191.

"Chemicals Produced in a Commercial Fischer–Tropsch Process," Industrial Chemicals Via C, Processes, Chapter 2, M.E. Dry, American Chemical Society Journal, vol. 328, 1987.

"The Syntroleum Process" Promotional Flier, Aug. 1994.

International Search Report, Re International Appln. PCT/US 10733, Oct. 17, 1997.

International Search Report dated Oct. 24, 1997 re International Application PCT/US97/10732, Oct. 24,1997.

"Conversion of Natural Gas to Liquid Fuels," R.C. Alden, The Oil and Gas Journal, Nov. 9, 1946, pp. 79–98, Nov. 9, 1946.

"Fischer–Tropsch Synthesis in Slurry Phase," M.D. Schlesinger, Industrial and Engineering Chemistry, Jun. 1951, pp. 1474–1479, Jun. 1985.

"Advances in low temperature Fischer–Tropsch synthesis," B. Jager & R. Espinoza, Catalysis Today, vol.23, 1995, pp. 17–28.

"Fischer–Tropsch Processes Investigated at the Pittsburgh Energy Technology Center since 1944," M.J. Baird, R.R. Schehl & WlP. Haynes, Ind. Eng. Chem. Prod. Res. Dev. 1980, pp. 175–191, 1980.

"Gasoline from Natural Gas," P.C. Keith, no date.

"Produce Diesel from Gas," A.H. Singleton, Hydrocarbon Processing, pp. 71–74, May 1983.

"Syn Gas from Heavy Fuels," C.J. Kuhre and C.J. Shearer, no date.

"Make Syn Gas by Partial Oxidation," C.L. Reed and C.J. Kuhre, Hydrocarbon Processing, Sep. 1979, pp. 191–194, Sep. 1979.

"Malaysia, Shell Mull Gas to Products Project," Oil & Gas Journal, p. 62, Sep. 16, 1985.

"Process Makes Mid–distillates from Natural Gas," Oil & Gas Journal, pp. 74–75, Feb. 17, 1986.

"The Magic of Designer Catalysts," Gene Bylinsky, Fortune, pp. 82–88, May 27, 1985.

"Syn Gas from Heavy Fuels," C.J. Kubre and C. J. Shearer, 1972.

SYNTHESIS GAS PRODUCTION SYSTEM AND METHOD

CROSS REFERENCE TO RELATED APPLICATIONS

This application is a divisional of U.S. application Ser. No. 08/879,553, filed Jun. 20, 1997 (Abandoned), by Kenneth L. Agee, Mark A. Agee, Larry J. Weick and Elliot L. Trepper and entitled "SYSTEM AND METHOD FOR CONVERTING LIGHT HYDROCARBONS TO HEAVIER HYDROCARBONS", as amended.

This application claims the benefit of U.S. Provisional Application Ser. No. 60/020,092, filed Jun. 21, 1996.

TECHNICAL FIELD OF THE INVENTION

The present invention relates to a system and method for converting light hydrocarbons into heavier hydrocarbons and more particularly to a conversion system having a combined autothermal reformer and turbine.

BACKGROUND OF THE INVENTION

Synthesis gas, or "syngas," is a mixture of gases prepared as feedstock for a chemical reaction; for example, carbon monoxide and hydrogen to make hydrocarbons or organic chemicals, or hydrogen and nitrogen to make ammonia. Syngas may be produced for use with a Fischer-Tropsch process, which is described further below and which is used as an example throughout.

The synthetic production of hydrocarbons by the catalytic reaction of carbon monoxide and hydrogen is known and is generally referred to as the Fischer-Tropsch reaction. Numerous catalysts have been used in carrying out the reaction, and at relatively low to medium pressure (near atmospheric to 600 psig) and temperatures in the range of from about 300° F. to 600° F., both saturated and unsaturated hydrocarbons can be produced. The synthesis reaction is very exothermic and temperature sensitive whereby temperature control is required to maintain a desired hydrocarbon product selectivity. The Fischer-Tropsch reaction can be characterized by the following general reaction:

$$2H_2 + CO \xrightarrow{Catalyst} -CH_2^- + H_2O$$

Two basic methods have been employed for producing the synthesis gas utilized as feedstock in the Fischer-Tropsch reaction. The two methods are steam reforming, wherein one or more light hydrocarbons such as methane are reacted with steam over a catalyst to form carbon monoxide and hydrogen, and partial oxidation, wherein one or more light hydrocarbons are combusted or reacted sub-stoichiometrically to produce synthesis gas.

The basic steam reforming reaction of methane is represented by the following formula:

$$CH_4 + H_2O \xrightarrow{Catalyst} CO + 3H_2$$

The steam reforming reaction is endothermic and a catalyst containing nickel is often utilized. The hydrogen to carbon monoxide ratio of the synthesis gas produced by steam reforming of methane is approximately 3:1.

Partial oxidation is the non-catalytic, sub-stoichiometric combustion of light hydrocarbons such as methane to produce the synthesis gas. The basic reaction is represented as follows:

$$CH_4 + \tfrac{1}{2}O_2 \rightarrow CO + 2H_2$$

The partial oxidation reaction is typically carried out using high purity oxygen. High purity oxygen can be quite expensive. The hydrogen to carbon monoxide ratio of synthesis gas produced by the partial oxidation of methane is approximately 2:1.

In some situations these approaches may be combined. A combination of partial oxidation and steam reforming, known as autothermal reforming, wherein air is used as a source of oxygen for the partial oxidation reaction has also been used for producing synthesis gas heretofore. For example, U.S. Pat. Nos. 2,552,308 and 2,686,195 disclose low pressure hydrocarbon synthesis processes wherein autothermal reforming with air is utilized to produce synthesis gas for the Fischer-Tropsch reaction. Autothermal reforming is a combination of partial oxidation and steam reforming where the exothermic heat of the partial oxidation supplies the necessary heat for the endothermic steam reforming reaction. The autothermal reforming process can be carried out in a relatively inexpensive refractory lined carbon steel vessel whereby low cost is typically involved.

The autothermal process results in a lower hydrogen to carbon monoxide ratio in the synthesis gas than does steam reforming alone. That is, as stated above, the steam reforming reaction with methane results in a ratio of about 3:1 while the partial oxidation of methane results in a ratio of about 2:1. The optimum ratio for the hydrocarbon synthesis reaction carried out at low or medium pressure over a cobalt catalyst is 2:1. When the feed to the autothermal reforming process is a mixture of light hydrocarbons such as a natural gas stream, some form of additional control is desired to maintain the ratio of hydrogen to carbon monoxide in the synthesis gas at the optimum ratio of about 2:1.

In producing a product from the synthesis unit, a residue gas is frequently produced. For some processes, the use of this gas to create energy has been suggested. Systems that have utilized the residue gas have required numerous additional components and steps to do so.

In producing a synthesis gas for the Fischer-Tropsch process or any other process, it is desirable to produce the synthesis gas as efficiently as possible. The ability to develop a process with low capital expense may be an imperative to development of large-scale systems.

SUMMARY OF THE INVENTION

Therefore, a need has arisen for a synthesis gas production system that addresses the shortcomings of the prior art. According to an aspect of the present invention, a synthesis gas production system includes a gas turbine with an autothermal reformer (ATR) interposed between the compressor and expander and wherein the ATR produces syngas and serves as the combustor for the gas turbine.

According to another aspect of the present invention, a system for converting lighter hydrocarbons to heavier hydrocarbons includes: a synthesis gas production unit having a compressor, an autothermal reformer fluidly coupled to the compressor for producing synthesis gas and reacting at least a portion the gas therein, and an expansion turbine fluidly coupled to the autothermal reformer for developing energy with the gas from the autothermal reformer; and a synthesis unit fluidly coupled to the expansion turbine for receiving the synthesis gas therefrom and producing heavier hydrocarbons.

According to another aspect of the present invention, a method of manufacturing synthesis gas production system includes providing a compressor, fluidly coupling an autothermal reformer to the compressor for producing synthesis gas and reacting at least a portion of the gas therein, and fluidly coupling an expansion turbine to the autothermal reformer for developing energy with the gas from the autothermal reformer.

A technical advantage of the present invention is that the system may obtain higher production of synthesis gas by running all or substantially all of the compressed air from the gas turbine through the autothermal reformer.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

The preferred embodiment of the present invention and its advantages are best understood by referring to FIGS. 1–5 of the drawings, like numerals being used for like and corresponding parts of the various drawings.

A. INTRODUCTION

The present invention involves the production of a synthesis gas, which may be used with synthesizing to produce methanol, DME, gasoline, or numerous other substances. As noted in the background, the invention is suitable for use to produce syngas for a Fischer-Tropsch reactor, methanol reactor, ammonia reactor, or reactors requiring synthesis gas. The invention is presented, however, in context of the Fischer-Tropsch process although it is to be understood that the application is much broader. A process flow in which the invention may be incorporated including the use of a turbine is first presented in connection with FIGS. 1 and 2, and then a couple of specific embodiments of the present invention are described in connection with FIGS. 3–5.

B. THE CONVERSION OF HEAVIER HYDROCARBONS FROM GASEOUS LIGHT HYDROCARBONS

Figure 1:
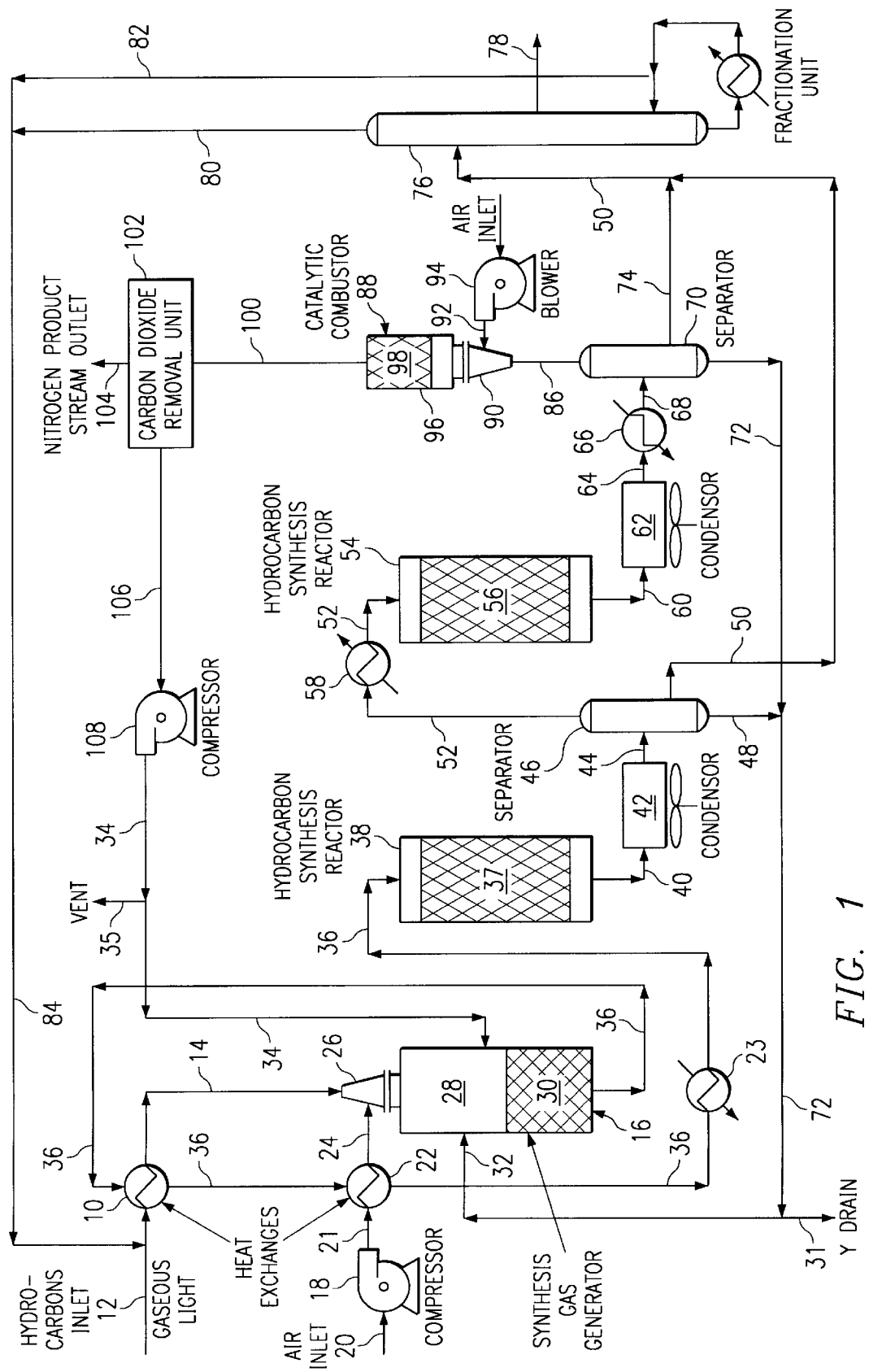
FIG. 1 is a schematic representation of a process flow in which the present invention is well suited.

The present invention may be used in the conversion of lighter hydrocarbons to heavier hydrocarbons. Referring to FIG. 1, one illustrative system for the conversion of heavier hydrocarbons from gaseous light hydrocarbons is shown. A continuous stream of gaseous light hydrocarbons, e.g., a natural gas stream, is conducted to a heat exchanger 10 of a conduit 12. While flowing through the heat exchanger 10, the stream of light hydrocarbons is heated by exchange of heat with a process stream of generated synthesis gas which as will be described below, comes from reactor 28. Typically, the feed stream of light hydrocarbons is at a pressure in the range of from near atmospheric pressure to 600 psig and is preheated in the heat exchanger 10 to a temperature in the range of from about 500° F. to about 1000° F. From the heat exchanger 10, the preheated feed stream is conducted by a conduit 14 to a synthesis gas generator, generally designated by the numeral 16.

Air is drawn to an air compressor 18 by way of an inlet conduit 20, and from the compressor 18, a stream of air is conducted to a heat exchanger 22 by a conduit 21. The stream of air is preheated in the heat exchanger 22 to a temperature in the range of from about 500° F. to about 1000° F. by exchange of heat with the synthesis gas stream exiting the heat exchanger 10. From the heat exchanger 22, the preheated air is conducted to the synthesis gas generator 16 by a conduit 24.

While the synthesis gas generator 16 can take various forms, it generally includes a burner 26 connected to one end of a reactor vessel 28. A bed of steam reforming catalyst 30, which typically contains nickel, is disposed within the reactor 28 at the end opposite the burner 26.

In this embodiment, the reactor 28 is a refractory lined carbon steel vessel. Steam or water, which instantly converts to steam, is introduced into the reactor 28 by way of a conduit 32 connected thereto, and optionally carbon dioxide may be introduced into the reactor 28 by way of a conduit 34 connected thereto.

In the operation of the synthesis gas generator 16, the preheated feed stream of gaseous light hydrocarbons from conduit 14 is intimately mixed with a preheated stream of air from conduit 24 in the burner 26 and ignited whereby the reaction takes place within the reactor 28. The combustion reaction is carried out at a temperature in the range of from about 1500° F. to about 2500° F. under sub-stoichiometric conditions whereby the light hydrocarbons are partially oxidized. A gas stream including nitrogen, unreacted light hydrocarbons, hydrogen and carbon monoxide is produced.

The unreacted light hydrocarbons in the combustion gas stream react with steam introduced into the reactor 28 in the presence of the reforming catalyst whereby additional hydrogen and carbon monoxide are produced therefrom. Simultaneously, carbon dioxide may be introduced into the reactor 28 to react with unreacted light hydrocarbons to produce additional carbon monoxide and hydrogen. The resulting synthesis gas stream generated within the generator 16 includes hydrogen, carbon monoxide, carbon dioxide, nitrogen and unreacted light hydrocarbons, synthesis gas exits the reactor 28 by way of a conduit 36. The combustion and reforming reactions preferably occur as coexisting reactions that reach equilibrium in generator 16.

In order to control the ratio of hydrogen to carbon monoxide in the synthesis gas stream produced in the synthesis gas generator 16 at a ratio as close to 2:1 as possible, the rates of water introduced into the reactor 28 by way of the conduit 32 and carbon dioxide introduced by way of the conduit 34 are varied. That is, the ratio of hydrogen to carbon monoxide in the produced synthesis gas stream, or the composition of the feed light hydrocarbon stream, or both, are monitored and used as the basis for changing the flow rates of steam and carbon dioxide to the reactor 28 whereby a constant ratio of hydrogen to carbon monoxide at about 2:1 is maintained in the existing synthesis gas.

The synthesis gas product stream produced in the generator 16 is conducted by the conduit 36 through the heat exchanger 10, then through the heat exchanger 22 and then to the inlet connection of a first hydrocarbon synthesis reactor 38. Upon exiting the generator 16, the synthesis gas is at a temperature in the range of from about 1000° F. to about 2000° F. As the synthesis gas stream flows through the heat exchanger 10 on conduit 36 it gives up heat to the feed light hydrocarbon stream. The light hydrocarbon stream in conduit 14 is preheated to a temperature in the range of from about 500°0 F. to about 1000° F. In a like manner, as the synthesis gas stream flows through the heat exchanger 22 on conduit 36, it gives up heat to the air flowing to the generator 16 through conduit 24 whereby the air is also preheated to a temperature in the range of from about 500° F. to about 1000° F. Additional cooling of the synthesis gas stream is provided by a cooler or heat exchanger 23 disposed in the conduit 36 whereby the temperature of the synthesis gas entering the reactor 38 is then in the range of from about 350° F. to about 550° F.

In the hydrocarbon synthesis case, reactor 38 can take various forms, but in the embodiment shown is a tubular reactor containing a fixed bed 37 of hydrocarbon synthesis catalyst. The catalyst of bed 37 may be of cobalt supported on silica, alumina or silica-alumina material in an amount in the range of from about 5 to about 50 parts by weight of cobalt per 100 parts by weight of the support material. The catalyst may also contain in the range of from about 0.05 to about 1 parts by weight of ruthenium per 100 parts by weight of support material as a promoter.

The synthesis gas stream flows into and through the reactor 38. The gas is delivered by conduit 36 and carried on its way by conduit 40. As mentioned above, the temperature within the reactor 38 is in the range of from about 350° F. to about 550° F., and upon contact with the catalyst, hydrogen and carbon monoxide in the synthesis gas stream react to form heavier hydrocarbons and water.

The product stream produced in the reactor 38 exits the reactor by way of a conduit 40 connected thereto. Conduit 40 leads the stream to a condenser 42. While flowing through the condenser 42, the heavier hydrocarbons and water contained in the stream are condensed. From the condenser 42, a conduit 44 conducts the stream containing condensed components to a separator 46 wherein the condensed heavier hydrocarbons and water are separated and separately withdrawn. That is, the condensed water is withdrawn from the separator 46 by way of a conduit 48 connected thereto, and the condensed heavier hydrocarbons are withdrawn from the separator 46 by way of a conduit 50 connected thereto.

A residue gas stream from the separator 46 includes nitrogen and unreacted hydrogen, carbon monoxide, light hydrocarbons and carbon dioxide. A conduit 52 connected to the separator 46 leads the residue gas stream from the separator 46 to a second hydrocarbon synthesis reactor 54 containing a fixed bed 56 of a hydrocarbon synthesis catalyst, such as the one described above. The pressure and temperature of the gas stream flowing through the reactor 54 are maintained at approximately the same levels as the pressure and temperature within the reactor 38 by means of a heater or heat exchanger 58 disposed in the conduit 52 between the separator 46 and reactor 54. While flowing through the reactor 54, additional heavier hydrocarbons are formed from hydrogen and carbon monoxide in the residue gas stream and the resulting product stream exits the reactor 54 by way of a conduit 60 connected thereto. The conduit 60 leads the stream to a condenser 62 wherein heavier hydrocarbons and water contained therein are condensed. From the condenser 62, the stream containing condensed components is conducted to a chiller 66 of a refrigeration unit by a conduit 64 wherein additional hydrocarbons and water are condensed. The resulting stream is conducted from the chiller 66 to a separator 70 by a conduit 68 connected therebetween. Separator 70 will have water, heavier hydrocarbons, and residue gas exit through three conduits.

Water is withdrawn from the separator 70 by a conduit 72 connected thereto. The conduit 72 is in turn connected by way of conventional valves and controls (not shown) to the conduit 48, to a drain conduit 31 and to the conduit 32 previously described whereby all or part of the condensed water separated in the separators 46 and 70 is selectively conducted to the synthesis gas generator 16.

The condensed heavier hydrocarbons separated within the separator 70 are withdrawn therefrom by a conduit 74 which connects to the conduit 50 from the separator 46. The conduit 50 leads the heavier hydrocarbons from both the separators 46 and 70 to a conventional fractionation unit 76. A hydrocarbon product stream containing selected components is withdrawn from the fractionation unit 76 by way of a conduit 78 which conducts the product stream to storage or other location. Undesirable light and heavy hydrocarbon fractions produced in the fractionation unit 76 are withdrawn therefrom by conduits 80 and 82, respectively. The conduits 80 and 82 connect to a conduit 84 which conducts the undesirable hydrocarbons to the inlet conduit 12 where they mix with the feed stream of gaseous light hydrocarbons and are recycled.

The residue gas stream produced in the separator 70, which may include nitrogen and unreacted hydrogen, carbon monoxide, light hydrocarbons and carbon dioxide, is withdrawn therefrom by a conduit 86 which leads the residue gas stream to a catalytic combustor 88. The catalytic combustor 88 may include a burner 90 into which the residue gas stream is conducted.

A stream of air is conducted to the burner 90 by a conduit 92 connected to the discharge of an air blower 94. The residue gas stream from the separator 70 and the air conducted to the burner 90 are intimately mixed therein, ignited and discharged into a reactor 96 connected to the burner 90.

The reactor 96 contains a fixed bed of suitable nobel metal containing catalyst 98, e.g., platinum or palladium, for promoting and catalyzing the oxidation of the oxidizable components in the residue gas stream. As a result of such oxidation an oxidation product stream including carbon dioxide, water vapor and nitrogen is produced and withdrawn from the combustor 88 by a conduit 100 connected thereto. The conduit 100 optionally leads the product stream to a conventional carbon dioxide removal unit 102. Carbon dioxide and water are removed from the stream by the carbon dioxide removal unit 102 thereby producing a relatively pure nitrogen product stream which is conducted from the unit 102 by a conduit 104 to a location of sale, storage or further processing.

The carbon dioxide removed by the unit 102 is withdrawn therefrom by a conduit 106 which leads the carbon dioxide to a compressor 108. The discharge of the compressor 108 is connected by way of conventional valves and controls (not shown) to a vent 35 and to the conduit 34 previously described whereby all or part of the carbon dioxide is selectively introduced into the synthesis gas generator 16.

As previously described, the flow rates of the water conducted to the synthesis gas generator 16 by way of the conduit 32 and carbon dioxide conducted thereto by way of the conduit 34 are varied as is necessary to control the ratio of hydrogen to carbon monoxide in the synthesis gas stream produced to as close to 2:1 as possible. This in turn improves the efficiency of the hydrocarbon synthesis reactions carried out in the reactors 38 and 54. Further, the use of air, delivered by conduit 24, in the synthesis gas generator 16 as the source of oxygen for the partial oxidation reaction carried out therein produces nitrogen in the synthesis gas stream. Such nitrogen acts as a diluent in the hydrocarbon synthesis reactors 38 and 54 and prevents hot spots on the catalyst and further increases the efficiency of the hydrocarbon synthesis reactions. The nitrogen together with the additional nitrogen produced in the catalytic combustor 88, after carbon dioxide removal, form a relatively pure nitrogen product stream. In addition, the recycling of all or part of the optional carbon dioxide, which is transported in conduit 106 provides additional carbon for producing heavier hydrocarbons and increases overall process efficiency.

The system of FIG. 1 can include a gas turbine as will be further described below in connection with FIG. 2. As an example of one way the system of FIG. 1 can be configured, catalytic combustor 88, the burner 90, the blower 94, and air compressor 18 may be removed and replaced with a gas turbine. The gas turbine could include a combustor to burn the gas and the compressor section of the gas turbine could provide combustion air as blower 94 previously did and compressed air as compressor 18 previously did. Other examples will be given further below.

Figure 2:
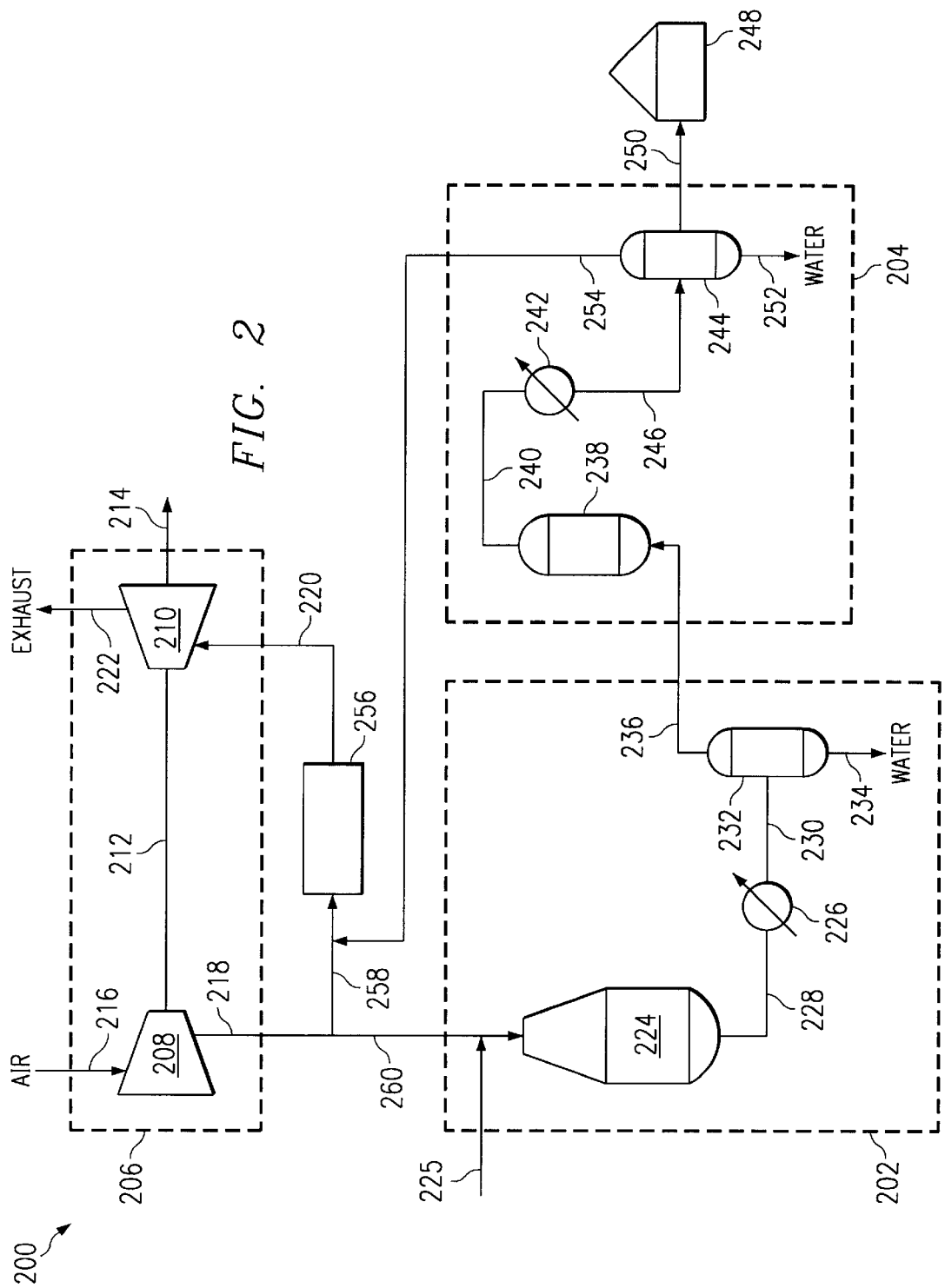
FIG. 2 is a schematic representation of a process flow showing a separate syngas reactor and turbine.

Referring now to FIG. 2, another illustrative system 200 for the conversion of lighter hydrocarbons to heavier hydrocarbons is shown. System 200 combines a synthesis gas unit 202 with a synthesis unit 204 and a gas turbine 206. System 200 uses gas turbine 206 to provide power for the process at a minimum, but is preferably designed to provide at least some additional power.

Gas turbine 206 has a compressor section 208 and an expansion turbine section 210. The power generated by the expansion turbine section 210 drives the compressor section 208 by means of linkage 212, which may be a shaft, and any excess power beyond the requirements of compressor section 208 may be used to generate electricity or drive other equipment as figuratively shown by output 214. Compressor section 208 has inlet or conduit 216, where in the embodiment shown compressor 208 receives air. Compressor section 208 also has an outlet or conduit 218 for releasing compressed air. Expansion turbine 210 has inlet or conduit 220 and outlet or conduit 222. Outlet 218 of compressor section 208 provides compressed air to synthesis gas unit 202 through conduit 260.

Synthesis gas unit 202 may take a number of configurations, but in the specific embodiment shown, includes syngas reactor 224, which as shown here may be an autothermal reforming reactor. A stream of gaseous light hydrocarbons, e.g., a natural gas stream, is delivered to syngas reactor 224 by inlet or conduit 225. In some instances it may be desirable to use natural gas containing elevated levels of components, e.g., $N_2$, $CO_2$ He, etc. that reduce the BTU value of the gas in conduit 225. The synthesis gas unit 202 may also include one or more heat exchangers 226, which in the embodiment shown is a cooler for reducing the temperature of the synthesis gas exiting outlet 228 of syngas reactor 224. Heat exchanger 226 delivers its output to inlet 230 of separator 232. Separator 232 removes moisture which is delivered to outlet 234. It may be desirable in some instances to introduce the water in conduit 234 as steam to expansion turbine 210. Synthesis gas exits separator 232 through outlet or conduit 236. The synthesis gas exiting through outlet 236 is delivered to synthesis unit 204.

Synthesis unit 204 may be used to synthesize a number of materials as previously mentioned, but in the specific example here is used to synthesize heavier hydrocarbons as referenced in connection with FIG. 1. Synthesis unit 204 includes Fischer-Tropsch reactor 238, which contains an appropriate catalyst. The output of Fischer-Tropsch reactor 238 is delivered to outlet 240 from which it travels to heat exchanger 242 and on to separator 244.

The product entering separator 244 is first delivered to inlet 246. Separator 244 distributes the heavier hydrocarbons separated therein to storage tank or container 248 through outlet or conduit 250. Conduit 250 may include additional components such as a conventional fractionation unit as shown in FIG. 1. Water withdrawn from separator 244 is delivered to outlet or conduit 252. It may be desirable in some instances to deliver the water in conduit 252 as steam into expansion turbine 210. The residue gas from separator 244 exits through outlet or conduit 254.

System 200 includes a combustor 256. Combustor 256 receives air from compression section 208 delivered through conduit 258 which is fluidly connected to conduit 260 connecting outlet 218 with syngas reactor 224. The conduit 260 beyond the juncture with conduit 258 delivers bleed air to the autothermal reformer 224. Also, residue gas delivered by separator 244 into conduit 254 is connected to combustor 256. Residue gas within conduit 254 is delivered to conduit 258 and then to combustor 256. Intermediate conduit 260 and the connection of conduit 254 with conduit 258 may be a valve (not explicitly shown) for dropping the pressure delivered from compressor section 208 to combustor 256 in order to match the pressure in conduit 254 as necessary. The output of combustor 256 is delivered to expansion turbine 210. In some embodiments, combustor 256 may be incorporated as part of gas turbine 206 itself. Alternatively, the pressure in conduits 260 and 254 may be increased by a compressor to match or exceed the pressure requirements of combustor 256.

C. COMBINATION AUTOTHERMAL REFORMER AND TURBINE

Figure 3:
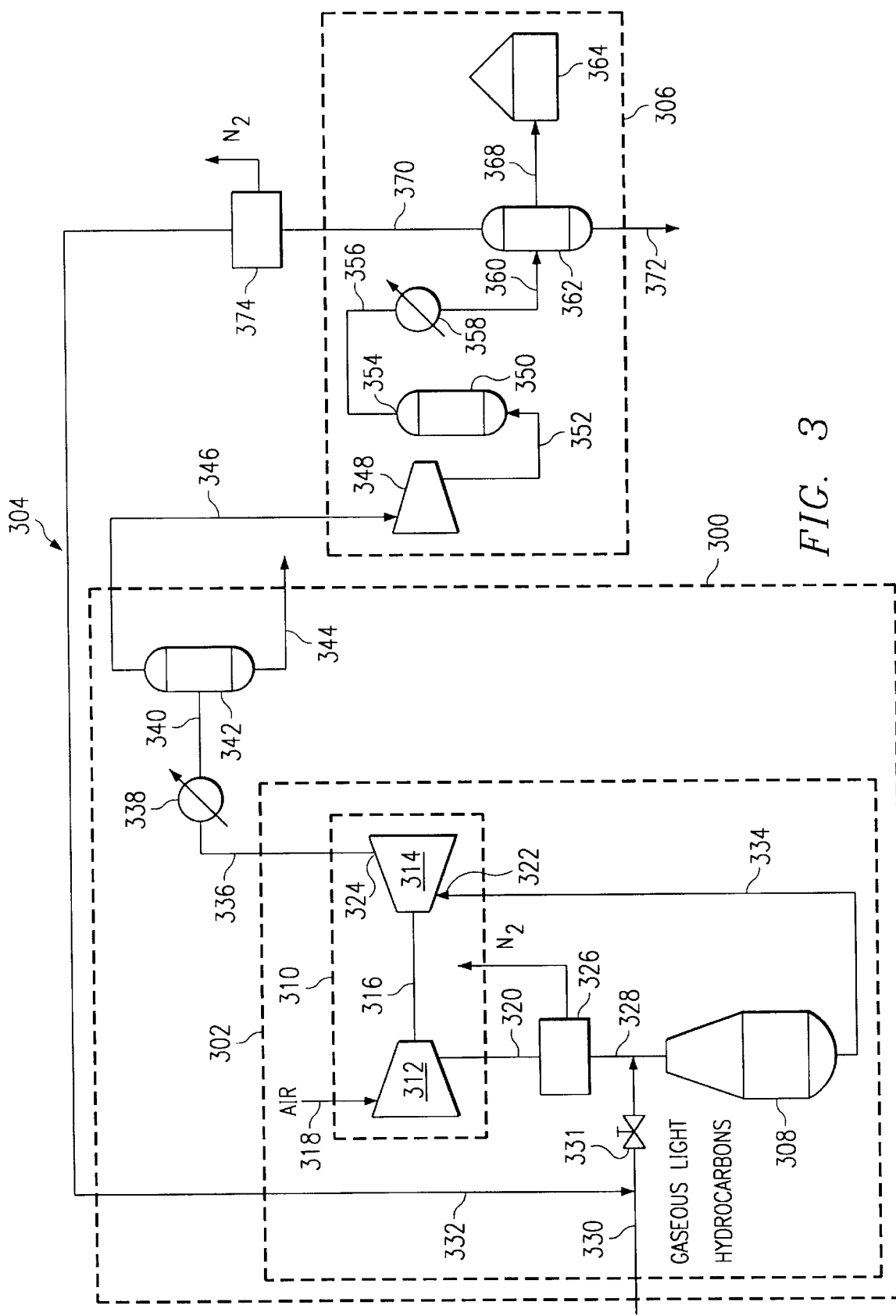
FIG. 3 is a schematic representation of a process flow showing an embodiment of the present invention with a combined syngas reactor and turbine.

Referring now to FIG. 3, there is shown a synthesis gas production system 300 according to an aspect of the present invention has an autothermal-reformer-turbine unit 302. Synthesis gas production system 300 may be included as part of system 304 for converting lighter hydrocarbons that further includes a synthesis unit 306.

Figure 4:
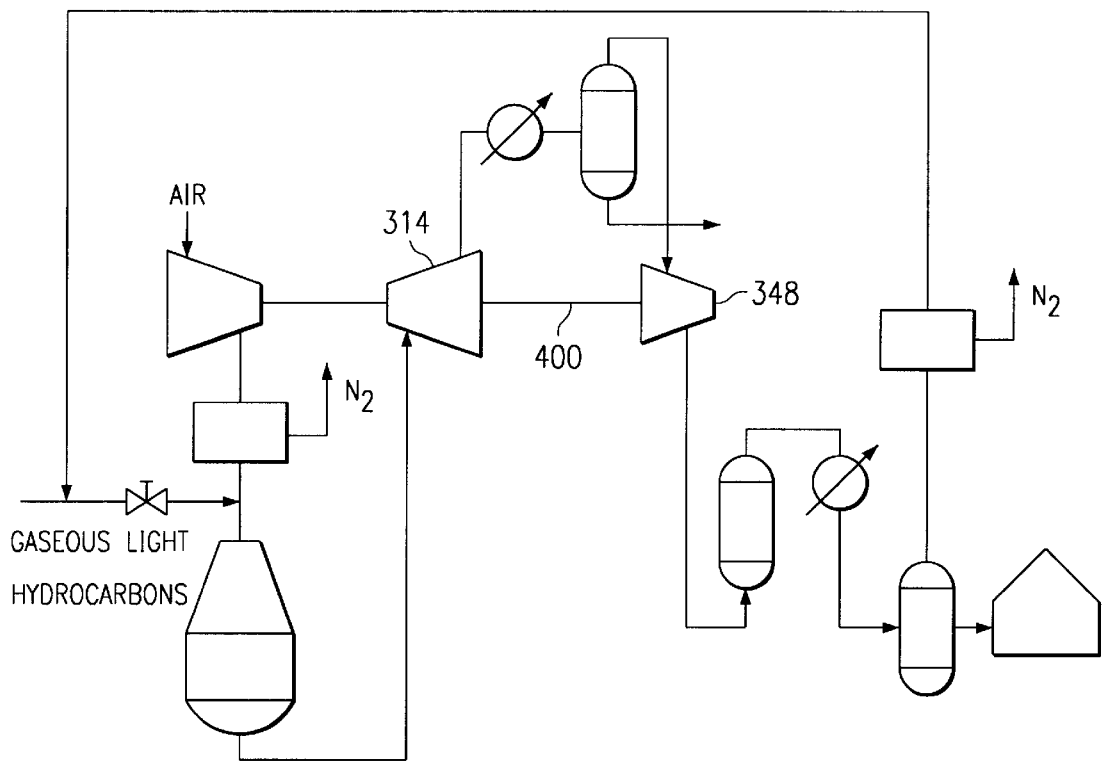
FIG. 4 is a schematic representation of a process flow showing a second embodiment of the present invention with a combined syngas reactor and turbine.

Autothermal-reformer-turbine unit 302 includes an autothermal reformer (ATR) 308 and gas turbine 310. Gas turbine 310 includes a compressor section 312 and an expansion turbine section 314. The power generated by the expansion turbine section 314 drives the compressor section 312 by means of linkage 316, which may be a shaft. This embodiment preferably has an exact energy balance, but if excess energy is developed, it may be removed from gas turbine 310 with an additional shaft extending from expansion section 314 as shown in FIG. 4. Compressor section 312 has inlet or conduit 318, where compressor 312 receives air. Compressor 312 also has an outlet or conduit 320 for releasing compressed air. The expansion turbine section 314 has inlet or conduit 322 and outlet or conduit 324. Outlet 324 of expansion section 314 provides compressed synthesis gas into conduit 336.

Autothermal reformer 308 produces synthesis gas, but also serves as the combustor of gas turbine 310. Compressor section 312 develops compressed air that is delivered to outlet 320, which is delivered to first separator 326, which will be described further below. After traveling through separator 326, compressed air is delivered by way of conduit 328 to ATR 308. In addition, gaseous light hydrocarbons, such as natural gas, are delivered to conduit 328 from conduit 330 and the residue gas is also delivered through conduit 332 into a portion of conduit 330 and then to conduit 328 and ATR 308.

An issue in the performance of gas turbines is the balancing of the axial loads on the shaft between the compressor section and the expansion section. The present invention may realize the most efficient results by the inclusion of thrust bearings in gas turbine 310 that allow for a substantial imbalance between compressor section 312 and expansion section 314. In order to use a preexisting turbine, however, unit 302 may provide for balancing of the loads within the turbine manufacturer's specifications. This may be accomplished with first separator 326 or by bleeding air as will be described. The balancing, may be thought of as balancing the mass that is received in the compressor section with the mass received by the turbine section or some percentage thereof.

In the present invention, unit 302 receives additional mass from conduits 330 and 332 between compressor section 312 and expansion section 314 that would cause an imbalance without provisions being made. To address this, separator 326 may remove mass by separating out nitrogen or bleeding off a portion of the compressed air as suggested by FIG. 3. Separator 326 may include separation technology such as a membrane or carbon absorption or any other technique suitable for the removal of nitrogen or other substances not needed by ATR 308. In embodiments with sufficiently strong thrust bearings in compressor 312 and turbine 314, no separator 326 or device for bleeding air is required.

ATR 308 will receive air and/or enriched air from conduit 328 along with the gaseous light hydrocarbons and residual gasses from conduits 330 and 332, respectively. ATR 308 will then autothermally reform the gas before delivering synthesis gas to conduit 334. The amount of gas delivered and produced by ATR 308 may be notably higher than that which would normally be expected from a normal gas-turbine combustor. ATR 308 does not fully combust or react the gas, but because of the larger volumes of gas delivered to ATR 308, an adequate amount of energy may be produced by expansion section 314. The ATR 308 will have an exit temperature in conduit 304 within an acceptable range for input into expansion section 314.

The gas delivered to ATR 308 may further be controlled to establish the proper ratios for ATR 308 such that the oxygen disappears and everything substantially goes to CO or $CO_2$. To control the gas that is delivered to ATR 308, one or more control valves, which are represented by control valve 331, may be used to control the ratio of gaseous light hydrocarbons to air entering ATR 308.

Outlet 324 of expansion section 314 delivers its products to conduit 336 which fluidly connects with heat exchanger or cooler 338. Then, the process continues from cooler 338 to conduit 340 and second separator 342. The synthesis gas, which will contain some combustion products and/or a nitrogen diluted gas, is delivered to expansion section 314 and expanded before exiting outlet 324. Cooler 338 further cools the gas which will condense at least some water from the gas. In this example, a Fischer-Tropsch process is presented, and the separator 342 will be desirable. The water condensed by the gas as it travels through the expansion section 314 and cooler 338, should be removed prior to delivering the product to second compressor 348. Thus, separator 342 includes drain 344 for the removal of water. The gaseous product leaving separator 342 is delivered by conduit 346 to compressor 348.

The syngas exiting expansion section 314 of gas turbine 310 may need to be pressurized before entering the Fischer-Tropsch reactor 350, and thus, compressor 348 may be added. Separator 342 removed the liquids that may have condensed prior to the compressor 348. Compressor 348 may be driven in a number of different ways. If the thrust bearings of gas turbine 310 allow for a sufficient imbalance for gas turbine 310 to create excess energy, a direct linkage 400 between expansion section 314 and compressor 348 may be utilized as shown in FIG. 4. If excess energy is not available from gas turbine 310 in adequate quantities, the excess energy may be used along with a supplement.

Compression in compressor 348 should adequately heat the gas existing to conduit 352 sufficiently for entry into Fischer-Tropsch reactor 350. The input to reactor 350 is preferably in the general range of 350° F. to 500° F. In some situations, it may be desirable to add a heat exchanger between compressor 348 and Fischer-Tropsch reactor 350 to further heat the gas therein.

Conduit 352 fluidly connects compressor 348 with reactor 350. Reactor 350, for this example, may be a Fischer-Tropsch reactor which contains an appropriate catalyst. Other reactors may be used with other processes as previously noted. The output of Fischer-Tropsch's reactor 350 is delivered to outlet 354 of conduit 356 connecting with heat exchanger 358. After heat exchanger 358, the product is delivered via conduit 360 to third separator 362. The heavier hydrocarbons separated in separator 362 are then delivered to storage tank or container 364 by conduit 368. The residual gas is delivered to conduit 370. Separator 362 will also remove water which is delivered to conduit 372 for the case of a Fischer-Tropsch process.

Conduit 370 delivers the residual gas to separator 374, which utilizes a separation process such as a membrane or carbon absorption or centrifugal process or other separation devices. For the instance of the Fischer Tropsch example, nitrogen may be removed from the methane. The output of separator 374 is delivered into conduit 332, which as previously noted delivers to ATR 308. In the preferred embodiment, the residual gas is completely consumed back into ATR 308 since the energy balance of the system is zero, or even a slight amount of additional energy is needed for a second compressor 348.

Figure 5:
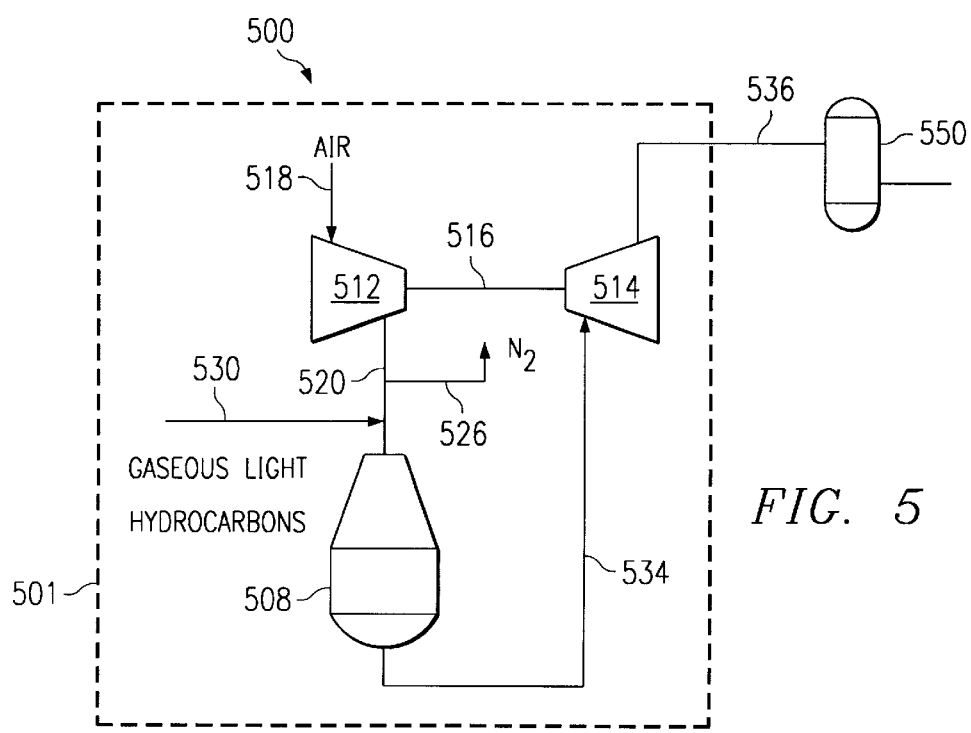
FIG. 5 is a schematic representation of a process flow showing a third embodiment of the present invention with a combined syngas reactor and turbine.

Referring now to FIG. 5, there is shown another embodiment of the present invention. Fischer-Tropsch system 500 includes synthesis gas production system 501 and a Fischer-Tropsch reactor 550. In this embodiment, compressed air is delivered through conduit 518 to compressor 512. Compressor 512 delivers compressed air to conduit 520. Conduit 520 delivers compressed air to autothermal reformer 508. Gaseous light hydrocarbons are delivered to conduit 520 and ultimately to ATR 508 by conduit 530. Because the addition of mass to the flow between compressor 512 and turbine 514, the thrust bearings associated with link 516 between compressor 512 and turbine 514 must be adequate to handle the imbalance, or a sufficient amount of mass will need to be removed to allow the thrust bearings to be within their specifications for an imbalance force. To remove the mass, if required, a separator removing nitrogen or a mechanism for bleeding a portion of the compressed air may be installed on conduit 520 as shown by reference numeral 526. The synthesis gas exiting ATR 508 is delivered to turbine 514 by conduit 534. The gas exiting turbine 514 enters conduit 536, which delivers it to Fischer-Tropsch's reactor 550. In this embodiment, the turbine may decrease the pressure of a synthesis gas entering turbine 514 down to a lesser, non-zero number as it exits into conduit 536. For example, it may exit at 50 psi before being delivered to reactor 550. While a higher pressure may be desired for reactor 550, sufficiently active catalysts may be utilized in reactor 550 such that the performance of reactor 550 is adequate at the lower pressure. This system will obviate the need for a second compressor. Thus, while reactor 550 may not perform at optimum output, the reduced capital cost of removing a compressor may make operation in this mode desirable.

Although the present invention has been described in detail with respect to alternative embodiments, various changes and modifications may be suggested to one skilled in the art, and it should be understood that various changes, substitutions and alterations can be made hereto without departing from the spirit and scope of the invention as defined by the appended claims.

What is claimed is:

1. A synthesis gas production system comprising:

a compressor for compressing air or enriched air;

an autothermal reformer fluidly coupled to the compressor and having a gaseous light hydrocarbon inlet, the autothermal reformer for producing synthesis gas;

an expansion turbine section fluidly coupled to the autothermal reformer for receiving synthesis gas from the autothermal reformer and developing energy with synthesis gas from the autothermal reformer; and a separator fluidly coupled between the compressor and autothermal reformer for removing mass from the compressed air or enriched air flowing therethrough.

2. The system of claim 1 wherein the compressor and expansion turbine comprise a single gas turbine.

3. A method of manufacturing a synthesis gas production system comprising the steps of:

providing a compressor for compressing air or enriched air;

providing a light hydrocarbon inlet;

fluidly coupling an autothermal reformer to the compressor and light hydrocarbon inlet, the autothermal reformer provided for producing synthesis gas and reacting at least a portion of the synthesis gas in the autothermal reformer; and fluidly coupling an expansion turbine section to the autothermal reformer for receiving synthesis gas from the autothermal reformer and developing energy with the synthesis gas from the autothermal reformer; and fluidly coupling a separator between the compressor and autothermal reformer for selectively removing mass from the compressed air or enriched air flowing to the separator.

4. The method of claim 3 wherein the step of fluidly coupling a separator between the compressor and autothermal reformer for selectively removing mass comprises the step of fluidly coupling a nitrogen separator between the autothermal reformer and compressor for removing nitrogen from the compressed air or enriched air flowing through the separator.

5. A synthesis gas production system comprising:

a compressor for compressing air or enriched air;

an autothermal reformer fluidly coupled to the compressor and having a gaseous light hydrocarbon inlet, the autothermal reformer for producing synthesis gas;

an expansion turbine section fluidly coupled to the autothermal reformer for receiving synthesis gas from the autothermal reformer and developing energy with synthesis gas from the autothermal reformer;

a separator fluidly coupled between the compressor and autothermal reformer for removing mass from the compressed air or enriched air flowing therethrough; and wherein the separator comprises a nitrogen separator fluidly coupled to the compressor and autothermal reformer for removing nitrogen from the gas flow therethrough.

* * * * *